United States Patent [19]

Ragland et al.

[11] Patent Number: 5,004,607

[45] Date of Patent: Apr. 2, 1991

[54] METHOD OF IMMUNIZING POULTRY

[75] Inventors: William L. Ragland; Mohamed G. Elfaki, both of Athens, Ga.

[73] Assignee: University of Georgia Research Foundation, Inc., Athens, Ga.

[21] Appl. No.: 296,319

[22] Filed: Jan. 11, 1989

Related U.S. Application Data

[63] Continuation of Ser. No. 89,350, Aug. 25, 1987, abandoned.

[51] Int. Cl.$^{5}$ .......................... A61K 39/00; C12N 1/00

[52] U.S. Cl. .......................................... 424/88; 424/92; 435/243; 435/252.1; 435/258

[58] Field of Search .................... 424/88, 92; 435/243, 435/252.1, 258

[56] References Cited

U.S. PATENT DOCUMENTS

| | | | |
|---|---|---|---|
| 3,147,186 | 9/1964 | Edgar . | |
| 3,917,819 | 11/1975 | Yoshioka et al. | 424/88 |
| 4,301,148 | 11/1981 | Shibata et al. . | |
| 4,438,097 | 3/1984 | Shirley . | |

OTHER PUBLICATIONS

Koski et al., "Inactivation of Mycoplasma by Use of Phenol, Formalin and Beta-Propiolactone", Chemical Abstracts, vol. 85, 1976, p. 40728, Ref. #40726c.

Levisohn et al., "A Quantitative Study of Single and Mixed Infection of the Chicken Trachea by *Mycoplasma gallisepticum*", Biological Abstracts, vol. 83(10): AB-488, Ref. #97284.

Lin et al., "Preparation and Evaluation of *Mycoplasma gallisepticum Bacteria* and Live Vaccines", Biological Abstracts, vol. 84(10): AB-449, Ref. #98101.

Karaca et al., "An Inactivated Temperature-Sensitive *Mycoplasma Gallisepticum* Mutant for Protection Against Airsacculitis", Biological Abstracts, vol. 84, (11): AB-54, Ref. #108361.

Sasaki et al., "Vaccines for *Mycoplasma gallisepticum* Infection in Chickens", Chemical Abstracts, vol. 88, p. 234, Ref. #65966f, 1978.

Frey et al., "A Medium for the Isolation of Avian Mycoplasmas", Am. J. Vet. Res., vol. 29, No. 11, pp. 2163-2171, 1968.

Adam, A., Synthetic Adjuvants, (John Wiley & Sons, Inc.), pp. 1 through 21; 56 through 58; 144 through 152 (1985).

Thomson et al., "Carrageenan: A Review of Its Effects on the Immune System", *Agents and Actions,* vol. 11, pp. 265-273 (1981).

Hildebrand, D. G., et al., "*Mycopolasma gallisepticum* (MG)—Laboratory and Field Studies Evaluating the Safety and Efficacy of an Inactivated MG Bacterin", *Avian Diseases,* vol. 27, pp. 792 through 802, (1983).

Yoder, Jr., H. W. et al., "Evaluation of Inactivated *Mycoplasma gallisepticum* Oil-Emulsion Bacterins for Protection Against Airsacculitis in Broilers", *Avian Diseases,* vol. 28, pp. 224 through 234 (1983).

Dolfi, A., et al., "Toxic Effect of Carrageenan on Lymphoid Follicle Associated Epithelial Cells of the Bursa of Fabricius of Chickens", *Cell Tissue Res.,* vol. 221, pp. 67 through 75, (1981).

Hayatsu, E., et al., "Local Immunization in Chicken Respiratory Tract with Killed *Mycoplasma gallisepticum* Vaccine", Jap. J. Vet. Sci., vol. 36, pp. 311 through 319, (1974).

Kleven, S. H. et al., "Bacterins and Vaccines for the Control of *Mycoplasma gallisepticum*", *Israel Journal of Medical Sciences,* vol. 20, pp. 989 through 991 (1984).

Yagihashi, T. et al., "Antibody Responses in Sera and Respiratory Secretions from Chickens Infected with *Mycoplasma gallisepticum*", Avian Diseases, vol. 30, pp. 543 through 550, (1986).

McDermott, M. R. et al., "Evidence for a Common Mucosal Immunologic System", *The Journal of Immunology,* vol. 122, pp. 1892 through 1898 (1979).

Nicklin, S. et al., "Local and Systemic Immune Responses to Intestinally Presented Antigen", *Int. Arch. Allergy Appl. Immun.,* vol. 72, 87-90 (1983).

Fumimasa, S. et al., "Vaccines for Mycoplasma gallisepticum Infection in Chickens", *Chemical Abstracts,* vol. 88, Abstract No. 88: 65966f (1978).

Kemal, K. et al., "Effect of Temperature-Sensitive *Mycoplasma Gallisepticum* Vaccine Preparations and Routes of Inoculation on Resistance of White Leghorns to Challenge", *Biol. Abstr.* 83(6): AB-488 Immunology (Immunochemistry), Abstract No. 54497.

*Primary Examiner*—Margaret Moskowitz
*Assistant Examiner*—Abdel A. Mohamed
*Attorney, Agent, or Firm*—Vincent J. La Terza

[57] ABSTRACT

A method of immunizing chickens in which a vaccine preparation containing both an inactivated mycoplasma and an adjuvant which stimulates the mucosal immune system is administered to chickens intracoelomically. Preferably, the vaccine preparation is subsequently administered to the chickens intranasally, intrabursally or intratracheally. The preferred adjuvant is iota carrageenan.

14 Claims, No Drawings

METHOD OF IMMUNIZING POULTRY

This is a division of application Ser. No. 089,350, filed Aug. 25, 1987, now abandoned.

TECHNICAL FIELD

The present invention relates to an improved method of immunizing poultry by administering an intracoelomic inoculation of antigen to poultry, and more particularly relates to a method of immunizing poultry by first inoculating poultry intracoelomically with a vaccine preparation and, subsequently, inoculating the poultry a second time with the vaccine preparation by either intrabursal, intranasal or intratracheal administration.

BACKGROUND ART

Coccidiosis is a parasitic disease of the intestinal tract of chickens. This disease has become widespread among commercial poultry institutions and is responsible for the death of millions of chickens each year. Chickens that survive the disease are often emaciated and sickly and are unsuitable for food consumption or egg laying for a prolonged period of time.

*Mycoplasma gallisepticum* is an organism that causes a chronic respiratory disease in poultry. This disease, like coccidiosis, is responsible for severe economic losses within the poultry industry.

Coccidial infections of the intestinal tract and mycoplasmal infections of the respiratory tract of the chicken occur primarily in epithelial cells of the mucosae. The organisms do not invade deeply enough to cause systemic infections. Consequently, the main line of defense should be at the mucosal surface in the form of secretory antibody or cell-mediated immunity. Attenuated strains of coccidia have been administered orally to chickens, but only partial immunization to pathogenic coccidia has been achieved.

Although the preferred method for the control of mycoplasma in poultry flocks is eradication of the organism in the poultry flocks, vaccination is another possible means to control the disease. An attenuated strain of mycoplasma has been used to vaccinate chickens by respiratory exposure. However, the attenuated strain does cause mild, transitory disease. Furthermore, the attenuated vaccine persists in the environment. The U.S. Department of Agriculture has been reluctant to approve such an attenuated vaccine because of its prolonged existence in the environment and the potential to revert to a virulent strain.

The U.S. Department of Agriculture has approved several vaccines comprising inactivated or killed mycoplasma, but, because these vaccines are administered parenterally, mucosal immunity is not adequately stimulated. Even though losses are reduced by vaccination, infection and the persistence of pathogenic strains occur.

What is needed is a vaccine comprising a non-viable organism or part of an organism that can stimulate adequate levels of mucosal immunity. Adequate stimulation should best be achieved by inoculation of the mucosal surfaces. However, numerous attempts to do this by exposing respiratory mucosae to killed mycoplasma have failed. Traditional adjuvants cannot be used with these vaccines because they would cause excessive irritation of the extremely sensitive respiratory and conjunctival mucosae.

Therefore, an improved method of vaccinating poultry by successfully exposing mucosae to a vaccine preparation is needed.

SUMMARY OF THE INVENTION

In accordance with the present invention, an improved method of immunizing chickens against a disease is provided comprising the steps of first inoculating said chickens with a vaccine preparation, wherein the first inoculation is intracoelomic and subsequently inoculating said chickens with the vaccine preparation.

Preferably, the improved method comprises a first intracoelomic inoculation of inactivated mycoplasma or a protein extracted from coccidia combined with adjuvant followed by a subsequent inoculation of inactivated mycoplasma combined with adjuvant, wherein the subsequent inoculation may be administered either intrabursally, intratracheally or intranasally.

The vaccine preparation preferably comprises an adjuvant that stimulates the mucosal immune system such as a muramyl dipeptide. The preferred adjuvant is iota carrageenan.

The vaccine preparation is preferably first administered at approximately three weeks of age and is subsequently administered at approximately five weeks of age. The vaccine preparation preferably immunizes chickens against such parasitic diseases as coccidiosis and disease caused by *Mycoplasma gallisepticum* organisms.

Accordingly, it is an object of the present invention to provide an improved method of immunizing poultry against poultry diseases such as coccidiosis and those caused by *Mycoplasma gallisepticum* organisms.

Another object of the present invention is to provide an improved method of immunizing poultry against poultry diseases wherein the main line of defense is at the mucosal surface.

Another object of the present invention is to provide an improved method of immunizing poultry against poultry diseases wherein the organism used in the vaccine does not persist in the environment.

Another object of the present invention is to provide an improved method of immunizing poultry against poultry diseases wherein the potential of the vaccine to revert to a virulent strain is precluded.

Another object of the present invention is to provide an improved method of immunizing poultry against poultry diseases wherein protection at mucosal surfaces is provided.

Another object of the present invention is to provide an improved method of immunizing poultry against poultry diseases while using an adjuvant, wherein excessive irritation of the sensitive respiratory and conjunctival mucosae is prevented.

Another object of the present invention is to provide an improved method of immunizing poultry against *Mycoplasma gallisepticum* organisms wherein eradication of the mycoplasma organism may be achieved.

These and other objects, features and advantages of the present invention will become apparent after a review of the following detailed description of the disclosed embodiment and the appended claims.

DETAILED DESCRIPTION OF THE DISCLOSED EMBODIMENT

In accordance with the present invention, an improved method of immunizing poultry against disease is provided wherein the mucosa (serosa) of the coelom is exposed to a vaccine. The vaccine may include an adjuvant.

The first disclosed method of the present invention comprises a first intracoelomic inoculation of an inactivated mycoplasma combined with an adjuvant that stimulates the mucosal immune system. It has been determined that the preferred adjuvant is a carrageenan, most preferably iota carrageenan, or a muramyl dipeptide, such as is commercially available as Regressin TM-(Vetrepharm Research, Inc., Athens, Ga.). The first inoculation is preferably administered at approximately 3 weeks of age but the first inoculation may be at any age earlier than 6 weeks of age.

The first inoculation is followed by a second inoculation of the inactivated mycoplasma combined with adjuvant. This second inoculation is preferably administered at approximately 5 weeks of age or 1 to 4 weeks after the first inoculation. The route of administration may be either intrabursal, intratracheal or intranasal. However, the preferred route of the second administration is intranasal. It will be understood by those skilled in the art that the route of the second administration could also be conjunctival or per os.

Preferably, the inactivated mycoplasma comprises a suspension of *Mycoplasma gallisepticum* cells inactivated by physical or chemical methods known by those of ordinary skill in the art. Most preferably the cells are inactivated chemically with formaldehyde. The inactivated cells are suspended in a solution containing approximately 0.1 to 0.3% iota carrageenan in phosphate buffer solution to give a 4–6% packed cell volume of *Mycoplasma gallisepticum* cells. This suspension comprises the preferred vaccine preparation.

Each bird is first inoculated intracoelomically with a dose containing approximately 0.05 to 0.2 ml of the vaccine. This dose is administered preferably at approximately 3 weeks of age.

A second inoculation containing the same dose, approximately 0.05 to 0.2 ml of the vaccine, is administered preferably at approximately 5 weeks of age. The second inoculation is preferably administered intranasally. However, the second inoculation may alternatively be administered intrabursally or intratracheally.

A second disclosed embodiment of the present invention comprises a protein extracted from coccidia organisms. The protein is combined with an adjuvant that stimulates the mucosal immune system as described above, preferably iota carrageenan.

The following specific examples will illustrate the invention as it applies in particular to treating coccidiosis and *Mycoplasma gallisepticum* diseases in poultry. It will be appreciated that other examples will be apparent to those of ordinary skill in the art and that the invention is not limited to these specific illustrative examples.

EXAMPLE 1

An experiment is conducted to analyze the effect of various adjuvants when used in combination with a coccidiosis vaccine.

Young chickens are inoculated intrabursally with a protein extracted from coccidia combined with the following adjuvants: Regressin TM (a mycobacterial cell wall fraction containing the immunostimulant muramyl dipeptide); one of the carrageenans; and Avridine TM (Pfizer Laboratories Division, NY, N.Y.) (an immunostimulant which has demonstrated potential for stimulating mucosal immunity by parenteral administration). Control groups are inoculated with saline or the protein without adjuvants.

The chickens are challenged with viable oocysts and immune protection is evaluated by weight gained over a four week period of time. The weight gain by the birds is compared with that of untreated, unchallenged chickens.

The untreated chickens and the chickens treated with saline, protein extract only, and the protein extract with Avridine TM fail to gain weight after challenge with viable, coccidial oocysts. The chickens treated with protein plus Regressin TM or carrageenan gain about half as much weight as the untreated, unchallenged chickens.

Because evaluation of weight gain is an established, sensitive and reliable method for measuring immunity to coccidia, it can be concluded that the mycobacterial (Regressin TM) and carrageenan adjuvants provided partial immunity to coccidia in the intestinal tract.

EXAMPLE 2

An experiment is conducted to examine the immunoprotective effects of various levels of the adjuvant iota carrageenan when used in combination with a *Mycoplasma gallisepticum* vaccine.

Newly hatched, male White Leghorn chickens free of Mycoplasma species and adventitious infections are placed in conventional chicken batteries and maintained free of said pathogens in a room supplied with filtered air under positive pressure. Unmedicated feed and water are provided ad libitum. Chickens are tagged with wing bands and randomly assorted to treatment (vaccination) and control groups at 3 weeks of age. At 7 weeks of age, all birds are infected with the virulent R strain of *Mycoplasma gallisepticum*, and transferred to a conventional chicken house where they are placed on a floor covered with soft, wood shavings. Unmedicated feed and water are provided ad libitum.

A suspension of virulent *Mycoplasma gallisepticum* (K781-R strain) at the eleventh passage in Frey's medium (Frey, M. L., R. P. Hanson, and D. P. Anderson, A Medium for the Isolation of Avian Mycoplasmas, Am. J. Vet. Res. 29:2163–2171, 1968.) is used for preparing vaccines and for challenge.

Freshly prepared Frey's medium is adjusted to pH 7.8 at 25° C. The medium is inoculated with 10% (V/V) of a 24 hour broth culture of the R strain *Mycoplasma gallisepticum* organisms, and incubated at 37° C. for 24 hours. Growth is monitored periodically by changes in pH.

When the pH reaches 6.5, 5 ml of the culture is taken for titration of colony forming units on solid agar nutrient medium, and *Mycoplasma gallisepticum* cells are harvested from the culture by centrifugation at 25,000× $g_{max}$ for 30 minutes at 4° C. The pellets are pooled in 0.01M phosphate buffered saline, pH 7.2, and washed four times by centrifugation. A final suspension is adjusted to contain 5% cells (packed cell volume) and inactivated with formalin (0.5% final concentration) at 37° C. for 3 hours with constant stirring. Sterility is confirmed by inoculating 0.1 ml into 1 ml Frey's medium which then is incubated at 37° C. for 10 days and plated onto solid agar nutrient medium.

Depending on the volume of vaccine needed, an appropriate volume of the inactivated *Mycoplasma gallisepticum* suspension is sedimented at 25,000× $g_{max}$ for 30 minutes at 4° C. The pellet is suspended in a sterile solution of 0.2% iota carrageenan (iCGN) in a phosphate buffer solution to give a 5% packed cell volume of *Mycoplasma gallisepticum* cells. A small volume of Thimerosal® (ICN Biomedicals, Inc., Costa Mesa, Calif.) is added to a final concentration of 0.001%. The Thimerosal® is added as a preservative and is optional. Protein concentration of vaccine preparation is determined according to Lowry et al. (Lowry, O. H., N. J. Rosebrough, A. L. Farr, and R. J. Randall, Protein measurement with the folin phenol reagent. *J. Biol. Chem.* 193:265–275, 1951) with a bovine serum albumin standard.

At necropsy, lesions in air sacs are graded on a scale of 0–4, according to published criteria (Kleven, S. H., D. D. King and D. P. Anderson, "Airsacculitis in broilers from Mycoplasma synoviae: effect on air-sac lesions of vaccinating with infectious bronchitis and Newcastle viruses." *Avian Dis.* 16:915–924, 1972.) without prior knowledge of treatment, and mean lesion scores are calculated. Comparisons among groups are also done by dividing the sum of scores from individual birds of each group by the sum of maximal scores possible (the sum of scores observed in the control group) to produce a lesion index for each group. A lesion index of 1.0 is the most severe change possible for an experimental group.

A preliminary experiment is conducted in a completely randomized design to study the protective effect of vaccines containing different concentrations of iota carrageenan as an adjuvant. The birds are randomly assorted to groups of equal numbers using a standard procedure. There are 8 chickens per group in this experiment. The experimental protocol is given below:

| Receive | Prime | Boost | Challenge | Necropsy |
|---|---|---|---|---|
| 1 day | 3 weeks | 5 weeks | 7 weeks | 9 weeks |

Three of five groups are treated with vaccines containing different concentrations of iota carrageenan (viz. 0.2, 0.5 and 1.0%). The three vaccine preparations are prepared from one batch of a laboratory vaccine and each contains 5% (packed cell volume) of inactivated *Mycoplasma gallisepticum* cells. Each chicken is vaccinated intracoelomically at 3 weeks of age with 0.1 ml vaccine, and intrabursally at 5 weeks of age by placing 0.1 ml of vaccine on the cloacal vent. A fourth group is given two separate 0.5 ml treatments of a commercially available, oil emulsion vaccine of inactivated *Mycoplasma gallisepticum* (Salsbury Laboratories, Charles City, Iowa) subcutaneously at 3 and 5 weeks of age. An untreated group is used for control. All of the birds are challenged with virulent *Mycoplasma gallisepticum* by aerosol exposure at 7 weeks of age. They are killed and subjected to postmortem examination at 9 weeks of age.

Lesion scores and indices are analyzed by analysis of variance using the Kruskal-Wallis test. Pairwise differences between them are evaluated using a nonparametric Tukey-type multiple comparisons technique. Relative numbers of chickens protected by treatment are compared with the unvaccinated chickens using Fisher's exact test.

In Table 1 it can be seen that the lowest level of iota carrageenan is at least as effective an adjuvant as the other 2 levels. On the basis of numbers of animals protected, it is the only group significantly different from the untreated group. Subsequent experiments, set forth in Examples 3 and 4, are performed with vaccine containing 0.2% iota carrageenan for this reason.

EXAMPLE 3

An experiment, employing a factorial design, is conducted to study the effect of bursal, tracheal and nasal routes of administration on the protective immunogenic effect of a vaccine containing 0.2% iota carrageenan in a phosphate buffer solution, using 3-week-old chickens. The materials and methods including experimental chickens, *Mycoplasma gallisepticum* organism, vaccine preparation, lesion scoring, experimental design and statistical analysis of Example 2 are employed. There are 16 chickens per group in this experiment.

A completely randomized experiment is performed to study the effect of each route of administration and the vaccine. Four of six groups are treated with the same batch of a laboratory vaccine containing 5% *Mycoplasma gallisepticum* cells and 0.2% iota carrageenan, 0.1 ml per dose. One group is given a single dose intrabursally (IB) at 3 weeks of age and another group is given a single dose intracoelomically (IC) at 3 weeks of age. A third group (IB/IB) is given one dose intrabursally at 3 weeks of age and another at 5 weeks of age. A fourth group (IC/IB) is given a priming dose intracoelomically at 3 weeks of age and a boosting dose intrabursally at 5 weeks of age. A fifth group is given commercial vaccine as in Example 2. An untreated group is used for control. All of the chickens are challenged, killed and examined as in Example 2.

Immunization by exposing bursal mucosae (Table 2) to the vaccine is ineffective even when a secondary exposure is used. A single intracoelomic (IC) injection results in significant resistance of the respiratory mucosa to challenge by virulent organisms, and the resistance is enhanced if the bursal mucosa is subsequently exposed. Primary intracoelomic exposure followed by secondary exposure of the bursal mucosae results in significant resistance to challenge and results in 75% protection from lesions of airsacculitis.

EXAMPLE 4

An experiment having an experimental design the same as in Example 3 is conducted except that intratracheal (IT) and intranasal (IN) routes of administration are substituted for intrabursal. There are 9 groups in this experiment: IC, IC/IT, IT, IT/IT, IC/IN, IN, IN/IN, Commercial vaccine and Control. There are 11 chickens per group in this experiment.

Immunization by exposing tracheal or nasal mucosae (Table 3) to the vaccine is ineffective even when a secondary exposure is used. A single intracoelomic (IC) injection results in significant resistance of the respiratory mucosa to challenge by virulent organisms, and the resistance is enhanced if the various mucosae are subsequently exposed. Although primary intracoelomic exposure followed by secondary exposure of the tracheal mucosae results in significant resistance to challenge, secondary exposure of the nasal mucosa (IC/IN) is most effective and results in 100% protection from lesions of airsacculitis.

It should be understood that the foregoing relates only to a preferred embodiment of the present invention and that numerous modifications or alterations may be made without departing from the spirit and scope of the invention as set forth in the appended claims.

TABLE 1

Adjuvant effect of iota carrageenan (iCGN) on intrabursal immunization of chickens with inactivated *Mycoplasma gallisepticum* (Mycoplasma) (Example 2).

| Treatment | Mean Lesion Score[a] | Lesion Index[b] | No. Protected[c]/ No. Challenged | % Protection |
|---|---|---|---|---|
| Mycoplasma + 1.0% iCGN | 0.50* | 0.22* | 5/8 | 63 |
| Mycoplasma + 0.5% iCGN | 0.50* | 0.22* | 4/8 | 50 |
| Mycoplasma + 0.2% iCGN | 0.13* | 0.06** | 7/8[d] | 88 |
| Commercial Vaccine | 0.38* | 0.17* | 5/8 | 63 |
| None (Control) | 2.25 | 1.00 | 1/8 | 13 |

[a]Severity of airsacculitis scored from 0–4, no lesions to most severe lesions
[b]Sum of lesion scores/sum of maximal lesion scores possible
[c]No. of chickens with no lesions in air sacs
[d]Different from untreated group at $p \leqq 0.05$, Fisher's exact test
*$p < 0.05$ by Kruskal-Wallis test when compared to untreated group
**$p < 0.01$ by Kruskal-Wallis test when compared to untreated group

TABLE 2

Comparison of Intracoelomic (IC) and Intrabursal (IB) Routes of Administration on Immunization with Inactivated *Mycoplasma gallisepticum* containing 0.2% Iota Carrageenan. (Example 3).

| Treatment | Mean Lesion Score[a] | Lesion Index[b] | No. Protected[c]/ No. Challenged | % Protection |
|---|---|---|---|---|
| IC | 0.83* | 0.50* | 6/12[d] | 50 |
| IC/IB | 0.25** | 0.15** | 9/12[d] | 75 |
| IB | 1.42 | 0.85 | 2/12 | 17 |
| IB/IB | 1.25 | 0.75 | 2/12 | 17 |
| Commercial Vaccine | 0.73* | 0.40* | 6/12[d] | 50 |
| None (Control) | 2.00 | 1.00 | 1/12 | 8 |

[a]Severity of airsacculitis scored from 0–4, no lesions to most severe lesions.
[b]Sum of lesion scores/sum of maximal lesion scores possible.
[c]No. of chickens with no lesions in air sacs.
[d]Different from untreated group at $p \leqq 0.05$, Fisher's exact test.
*$p < 0.05$ by Kruskal-Wallis test when compared to untreated group.
**$p < 0.01$ by Kruskal-Wallis test when compared to untreated group.

TABLE 3

Comparison of intracoelomic (IC), intratracheal (IT), and intranasal (IN) routes of administration on immunization with inactivated *Mycoplasma gallisepticum* containing 0.2% iota carageenan (Example 4)

| Treatment | Mean Lesion Score[a] | Lesion Index[b] | No. Protected[c]/ No. Challenged | % Protection |
|---|---|---|---|---|
| IC | 0.30* | 0.14* | 8/10 | 80 |

TABLE 3-continued

Comparison of intracoelomic (IC), intratracheal (IT), and intranasal (IN) routes of administration on immunization with inactivated *Mycoplasma gallisepticum* containing 0.2% iota carageenan (Example 4)

| Treatment | Mean Lesion Score[a] | Lesion Index[b] | No. Protected[c]/ No. Challenged | % Protection |
|---|---|---|---|---|
| IC/IT | 0.27* | 0.14* | 9/11[d] | 82 |
| IT | 1.36 | 0.68 | 4/11 | 36 |
| IT/IT | 1.45 | 0.73 | 3/10 | 30 |
| IC/IN | 0.00** | 0.00** | 11/11[d] | 100 |
| IN | 1.45 | 0.73 | 3/11 | 27 |
| IN/IN | 1.18 | 0.59 | 3/11 | 27 |
| Commercial Vaccine | 0.09* | 0.05** | 10/11[d] | 91 |
| None (Control) | 2.00 | 1.00 | 2/11 | 18 |

[a]Severity of airsacculitis scored from 0–4, no lesions to most severe lesions
[b]Sum of lesion scores/sum of maximal lesion scores possible
[c]No. of chickens with no lesions in air sacs
[d]Different from untreated group at $p \leqq 0.05$, Fisher's exact test
*$p < 0.05$ by Kruskal-Wallis test when compared to untreated group
**$p < 0.01$ by Kruskal-Wallis test when compared to untreated group

We claim:

1. An improved method of immunizing poultry against a disease comprising the steps of:
   (a) first inoculating the poultry with a poultry vaccine preparation, wherein the first inoculation is intracoelomic; and
   (b) subsequently inoculating the poultry with a poultry vaccine preparation.

2. The method of claim 1, wherein said subsequent inoculation is intranasal.

3. The method of claim 1, wherein said subsequent inoculation is intrabursal.

4. The method of claim 1, wherein said subsequent inoculation is intratracheal.

5. The method of claim 1, wherein said vaccine preparation further comprises an adjuvant.

6. The method of claim 5, wherein said adjuvant stimulates the mucosal immune system.

7. The method of claim 6, wherein said adjuvant is a muramyl dipeptide.

8. The method of claim 6, wherein said adjuvant is a carrageenan.

9. The method of claim 8, wherein said carrageenan is an iota carrageenan.

10. The method of claim 1, wherein said disease is a parasitic disease.

11. The method of claim 1, wherein said disease is coccidiosis.

12. The method of claim 1, wherein said disease is caused by *Mycoplasma gallisepticum* organisms.

13. The method of claim 1, wherein said first inoculation is administered to said poultry when said poultry are approximately three weeks of age.

14. The method of claim 1, wherein said subsequent inoculation is administered to said poultry when said poultry are approximately five weeks of age.

* * * * *